US009555403B2

(12) United States Patent
Kiss et al.

(10) Patent No.: US 9,555,403 B2
(45) Date of Patent: Jan. 31, 2017

(54) ACTIVATION AND USE OF HYDROALKYLATION CATALYSTS

(71) Applicant: ExxonMobil Chemical Patents Inc., Baytown, TX (US)

(72) Inventors: Gabor Kiss, Hampton, NJ (US); Tan-Jen Chen, Kingwood, TX (US); Thomas E. Green, Hamilton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 129 days.

(21) Appl. No.: 14/403,806

(22) PCT Filed: Jul. 9, 2013

(86) PCT No.: PCT/US2013/049720
§ 371 (c)(1),
(2) Date: Nov. 25, 2014

(87) PCT Pub. No.: WO2014/018251
PCT Pub. Date: Jan. 30, 2014

(65) Prior Publication Data
US 2015/0099910 A1  Apr. 9, 2015

Related U.S. Application Data

(60) Provisional application No. 61/675,027, filed on Jul. 24, 2012.

(51) Int. Cl.
| | | |
|---|---|---|
| B01J 29/74 | (2006.01) | |
| C07C 2/74 | (2006.01) | |
| B01J 37/18 | (2006.01) | |
| B01J 38/10 | (2006.01) | |
| B01J 38/56 | (2006.01) | |

(52) U.S. Cl.
CPC ............. B01J 29/7476 (2013.01); B01J 37/18 (2013.01); B01J 38/10 (2013.01); B01J 38/56 (2013.01); C07C 2/74 (2013.01); *B01J 2229/42* (2013.01); *C07C 2101/14* (2013.01); *C07C 2529/74* (2013.01); *Y02P 20/584* (2015.11)

(58) Field of Classification Search
CPC .............. C07C 2/74; C07C 2/73; C07C 13/18; B01J 29/74; B01J 29/70; B01J 29/76; B01J 29/7476
USPC .. 585/268; 502/85, 74, 38, 53, 489; 260/667
See application file for complete search history.

(56) References Cited

U.S. PATENT DOCUMENTS

| | | | |
|---|---|---|---|
| 3,238,120 A | | 3/1966 | Sale |
| 3,760,017 A | | 9/1973 | Arkell et al. |
| 3,760,018 A | | 9/1973 | Suggitt et al. |
| 3,926,842 A | * | 12/1975 | Suggitt .................... B01J 23/94 |
| | | | 502/38 |
| 4,268,699 A | | 5/1981 | Murtha et al. |
| 4,329,531 A | | 5/1982 | Murtha et al. |
| 5,053,571 A | | 10/1991 | Makkee |
| 6,037,513 A | * | 3/2000 | Chang ..................... B01J 29/72 |
| | | | 585/268 |
| 2011/0021841 A1 | | 1/2011 | Chen et al. |

FOREIGN PATENT DOCUMENTS

| | | |
|---|---|---|
| EP | 0 338 734 | 10/1989 |
| WO | WO 2009/021604 | 2/2009 |

OTHER PUBLICATIONS

Dietz, W. A., "*Response Factors for Gas Chromatography Analyses*," Journal of Gas Chromatography, Feb. 1967, vol. 5, pp. 68-71.
Koshel et al., "*Single-step method for hydrodimerization of benzene to phenylcyclohexane and some industrial syntheses based thereon*," Doklady Akademii Nauk SSR 237 (1977), pp. 164-167. (English Translation).
Slaugh et al., "*Hydromerization of benzene to phenylcyclohexane over supported transition metal catalysts*," Journal of Catalysis, 1969, vol. 13, Issue 4, pp. 385-396.

* cited by examiner

*Primary Examiner* — Sharon Pregler
(74) *Attorney, Agent, or Firm* — Stephen A. Baehl

(57) ABSTRACT

A process for activating a hydroalkylation catalyst in a first state comprising an acid component and a hydrogenating metal component, including: (i) treatment at a temperature of at least 120° C. in the presence of hydrogen for a first duration to produce a catalyst in a second state having a first hydroalkylation activity; (ii) contacting the catalyst in the second state with an aromatic compound and hydrogen under a hydroalkylation condition effective to convert at least part of the aromatic compound to a cycloalkylaromatic compound and produce a catalyst in a third state; and (iii) treating the catalyst in the third state at a temperature of at least 160° C. in the presence of hydrogen but advantageously in the substantial absence of the aromatic compound for a third duration to produce an activated catalyst in a fourth state having a third hydroalkylation activity greater than the first hydroalkylation activity.

25 Claims, No Drawings

ACTIVATION AND USE OF HYDROALKYLATION CATALYSTS

CROSS REFERENCE TO RELATED APPLICATIONS

This application is a National Stage Application of International Patent Application No. PCT/US2013/49720 filed Jul. 9, 2013, which claims priority to U.S. Provisional Application No. 61/675,027, filed Jul. 24, 2012, both of which are incorporated by reference.

FIELD

The present invention relates to the activation of hydroalkylation catalysts and to the use of the activated catalysts in producing cycloalkylaromatic compounds, in particular cyclohexylbenzene.

BACKGROUND

The production of cycloalkylaromatic compounds, such as cyclohexylbenzene, is a commercially important reaction since these compounds have utility as chemical feedstocks, solvents and industrial fluids.

Currently, the most common route for the production of phenol is the Hock process via cumene. This is a three-step process involving alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene. Thus, a process that does not require propylene as a feed and coproduces higher ketones, rather than acetone, may be an attractive alternative route to the production of phenol.

One such process involves the catalytic hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts.

An example of such a process is described in, for example, U.S. Pat. No. 3,760,017, which discloses a method for the catalytic hydroalkylation of an aromatic hydrocarbon, such as benzene, to cyclohexylbenzene using a dual function catalyst followed by the conversion of the cyclohexylbenzene to cyclohexanone and phenol by air oxidation and acid decomposition. The dual function catalyst comprises a Group VIII metal selected from the group consisting of cobalt, nickel and palladium, and an acidic oxide support consisting essentially of a substantially alkali metal-free mixture of about 5 wt % to 60 wt % of a crystalline zeolite, such as zeolite Y, and about 95 wt % to 40 wt % of a silica-alumina cracking catalyst. The dual function catalyst is produced by impregnating the support with a solution of the desired hydrogenation metal(s) followed by calcining in an oxidizing atmosphere to convert the hydrogenating component to the oxide form. The catalyst is then reduced, by contact with hydrogen for, e.g., 4.0 hours at 900° F. (482° C.). The resultant catalyst is shown to exhibit benzene conversions of 26.3% to 35.1% at a reaction temperature of 174-183° C. and a hydrogen pressure of 500 psig.

A further process is described in U.S. Pat. No. 6,037,513 (hereinafter the '513 Patent), in which an aromatic hydrocarbon, such as benzene, is contacted with hydrogen in the presence of a bifunctional catalyst which has both hydrogenation activity and alkylation activity. In particular, the catalyst comprises a metal having hydrogenation activity, such as palladium, and a crystalline inorganic oxide material having alkylation activity and an X-ray diffraction pattern including d-spacing maxima at 12.4±0.25, 6.9±0.15, 3.57±0.07, and 3.42±0.07 Angstrom. The crystalline inorganic oxide material may be composited with a binder or matrix. The catalyst is produced by impregnating the crystalline inorganic oxide material with an aqueous solution of a palladium salt and, then prior to employing the catalyst in a hydroalkylation reaction, treating the catalyst with 50 cc/min of flowing hydrogen for 2.0 hours at 300° C. and 1 atm pressure. Although not stated in the '513 Patent, this hydrogen treatment is employed to activate the catalyst by converting the palladium salt to a more active form of palladium.

Experience operating the process described in the '513 Patent has shown that the activated catalyst can convert about 34 wt % benzene in a single-pass through a fixed bed reactor nominally operating at 145° C., 165 psig (1138 kPa gauge) total pressure, 2.5 weight benzene/weight catalyst/hour weight-hourly space velocity (WHSV) with an $H_2$/benzene feed molar ratio of 0.7. Thus, at least 60 wt % of the benzene remains unconverted after each pass of the benzene feed through the hydroalkylation reactor. There is significant interest in increasing the benzene conversion of the catalyst provided this can be achieved without reducing its cyclohexylbenzene selectivity.

According to the present invention, it has now been found that the aromatic conversion activity of hydroalkylation catalysts, such as those disclosed in the '513 Patent, can be improved, desirably without reduction in cycloalkylaromatic selectivity by subjecting the catalyst to a second hydrogen activation treatment after the catalyst is exposed to a hydroalkylation condition between the first and second hydrogen treatments.

In this respect, it is known that catalysts, particularly supported metal catalysts, are sometimes exposed to hydrogen treatments after being on stream in a catalytic reaction in order to restore their lost activity. Such treatments are often referred to in the art of catalysis as rejuvenation. Such treatments, however, at best restore catalytic activity, but do not increase it above the start of run activity levels. In fact, while such treatments can restore some of the lost activity, they often cannot restore the full start of run activity. Surprisingly, the currently disclosed treatment results in a different outcome, namely, the catalyst treated by the three-step activation process of the current disclosure has higher activity than can be achieved by the prior-art one-step activation process.

SUMMARY

In one aspect, the present disclosure relates to a process for activating a hydroalkylation catalyst, the process comprising:

(a) providing a hydroalkylation catalyst in a first state comprising an acid component and a hydrogenating metal component;

(b) treating the catalyst in the first state at a first temperature of at least 120° C. in a first atmosphere comprising hydrogen and at most 5% by mole of an aromatic compound for a first duration to produce a catalyst in a second state having a first hydroalkylation activity HA1;

(c) contacting the catalyst in the second state with a first aromatic compound and hydrogen under a first hydroalkylation condition at a second temperature for a second duration effective to convert at least part of the first aromatic compound into a second aromatic compound comprising an alkyl group, and thereby obtaining a catalyst in a third state having a second hydroalkylation activity HA2; and (d) treating the catalyst in the third state at a third temperature of at least 160° C. in a third atmosphere comprising hydrogen and less than 30% by mole of the first aromatic compound for a third duration to produce a catalyst in a fourth state having a third hydroalkylation activity HA3, where HA3>HA1.

In a second aspect, the present disclosure relates to a process for producing a cycloalkyl substituted aromatic compound, the process comprising:

(a) providing a hydroalkylation catalyst in a first state comprising an acid component and a hydrogenating metal component;

(b) treating the catalyst in the first state at a first temperature of at least 120° C. in a first atmosphere comprising hydrogen and at most 5% by mole of an aromatic compound for a first duration to produce a catalyst in a second state having a first hydroalkylation activity HA1;

(c) contacting the catalyst in the second state with a first aromatic compound and a second atmosphere comprising hydrogen under a first hydroalkylation condition at a second temperature for a second duration effective to convert at least part of the first aromatic compound into a second aromatic compound comprising an alkyl group, and thereby obtaining a catalyst in a third state having a second hydroalkylation activity HA2;

(d) treating the catalyst in the third state at a third temperature of at least 160° C. in a third atmosphere comprising hydrogen and less than 30% by mole of the first aromatic compound for a third duration to produce a catalyst in a fourth state having a third hydroalkylation activity HA3, where HA3>HA1; and (e) contacting the catalyst in the fourth state in a hydroalkylation reactor with a third aromatic compound and hydrogen under a second hydroalkylation condition effective to convert at least part of the third aromatic compound to a fourth aromatic compound comprising a cycloalkyl group.

Desirably in certain embodiments, the hydrogenating metal component comprises at least one of Re, Fe, Ru, Os, Co, Rh, Ir, Ni, Pd, Pt, advantageously Pd, and the acid component comprises a molecular sieve, advantageously an MWW type zeolite.

Desirably in certain embodiments, the first atmosphere is a flowing stream of gas comprising $H_2$. Desirably in certain embodiments, the first atmosphere consists of dry $H_2$.

Desirably in certain embodiments, the second atmosphere is a flowing stream of gas comprising $H_2$. Desirably in certain embodiments, the second atmosphere consists essentially of $H_2$.

In one embodiment, the aromatic compound is benzene and the cycloalkylaromatic compound is cyclohexylbenzene.

DETAILED DESCRIPTION

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenating metal" include embodiments where one, two, or more hydrogenating metals are used, unless specified to the contrary or the context clearly indicates that only one hydrogenating metal is used. Likewise, "a first hydroalkylation condition" should be interpreted to include one first hydroalkylation condition at a specific pressure, flow rate, and the like, and multiple first hydroalkylation conditions involving a range of pressures, flow rates and other reaction parameters, and a plurality of reactor types.

As used herein, "wt %" means percentage by weight, "vol %" means percentage by volume, "mol %" means percentage by mole, "ppm" means parts per million, and "wt ppm" means parts per million on a weight basis.

The processes described herein can be advantageously used to activate a catalyst useful in the hydroalkylation of benzene and substituted benzenes, particularly alkyl-substituted benzenes, for example, ethylbenzene, toluene, xylenes to produce cycloalkylaromatic compounds. The thus activated catalyst can then be advantageously used in the processes for making cyclohexyl benzene and cyclohexyl substituted benzenes. The resulting cyclohexyl substituted benzenes can then be oxidized to produce corresponding hydroperoxides, which in turn can be cleaved to produce phenol and cyclohexanone or corresponding derivatives thereof.

Preparation and Activation of the Hydroalkylation Catalyst

The hydroalkylation catalyst employed in the present processes is a bifunctional catalyst comprising an acid component, such as a solid acid component, and a hydrogenating metal component, optionally together with an amorphous inorganic oxide support component.

Suitable solid acid components for the catalyst include mixed metal oxides, for example, tungstated zirconia, and zeolites, for example, zeolite beta, zeolite X, or Y, mordenite and zeolites having the MWW framework (see "Atlas of Zeolite Framework Types", Fifth edition, 2001). Molecular sieves of the MWW framework type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No.

WO97/17290), MCM-36 (described in U.S. Pat. No. 5,250, 277), MCM-49 (described in U.S. Pat. No. 5,236,575), MCM-56 (described in U.S. Pat. No. 5,362,697), UZM-8 (described in U.S. Pat. No. 6,756,030), and mixtures thereof. In one practical embodiment, the molecular sieve is selected from (a) MCM-22 and (b) MCM-49.

Any known hydrogenating metal component can be employed in the hydroalkylation catalyst, although suitable metals include palladium, platinum, ruthenium, iron, rhenium, rhodium, osmium, iridium, nickel, zinc, tin, and cobalt, with palladium being particularly advantageous. Advantageously, the amount of hydrogenating metal component present in the catalyst is from about 0.05 wt % to about 10 wt %, such as from about 0.1 wt % to about 5 wt %, of the catalyst. In one embodiment, where the MCM-22 family molecular sieve is an aluminosilicate, the molar ratio of the aluminum in the molecular sieve to the hydrogenating metal is from about 1.5 to about 1500, for example from about 75 to about 750, such as from about 100 to about 300.

The hydrogenating metal may be directly supported on the solid acid component by, for example, impregnation or ion exchange, or can be supported on the amorphous inorganic oxide component, or both. In one embodiment, at least 50 wt %, for example at least 75 wt %, and advantageously substantially all of the hydrogenating metal is supported on an amorphous inorganic oxide support component separate from but composited with the solid acid component. By supporting the hydrogenating metal on the amorphous inorganic oxide support, the activity of the catalyst and its selectivity to cyclohexylbenzene and dicyclohexylbenzene are increased as compared with an equivalent catalyst in which the hydrogenating metal component is supported directly on the solid acid component.

The amorphous inorganic oxide support employed in such a composite hydroalkylation catalyst is not narrowly defined, provided it is stable and inert under the conditions of the hydroalkylation reaction. Suitable inorganic oxides include oxides of Groups 2, 3, 4, 5 13, and 14 of the Periodic Table of Elements. Examples for suitable and widely available amorphous inorganic oxides include, for example, alumina, titania, and/or zirconia. As used herein, the numbering scheme for the Periodic Table Groups is as disclosed in Chemical and Engineering News, 63(5), 27 (1985).

Where the hydrogenating metal is deposited on the inorganic oxide support in various embodiments, this is desirably effected by impregnation with a solution of a salt of the desired metal, before the metal-containing inorganic oxide is composited with said solid acid component. In such embodiments, the catalyst composite is produced by co-pelletization, in which a mixture of the solid acid component and the metal-containing inorganic oxide is formed into pellets at high pressure (desirably about 350 kPa to about 350,000 kPa), or by co-extrusion, in which a slurry of the solid acid component and the metal-containing inorganic oxide, optionally together with a separate binder, are forced through a die. If necessary, additional hydrogenating metal can subsequently be deposited on the resultant catalyst composite.

In other embodiments, the crystalline solid acid is first extruded with the amorphous oxide as a binder, and then the metal is impregnated into the extrudate. In this case, the impregnation conditions can be adjusted such that the metal is preferentially associated with the amorphous oxide component of the extrudate.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Ga., and Florida clays or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

In certain embodiments, after producing the catalyst composite containing the hydrogenating metal component before activation, a catalyst precursor, i.e., a catalyst in the first state, is obtained. The hydrogenating metal supported on the acid component and/or the inorganic binder can be at least partly in oxidized state in the catalyst in the first state. For example, if the hydrogenating metal is deposited on the support in the form of a salt, the metal would be present at least partly in an ionic state before treatment in a reducing environment. For example, where impregnation by $PdCl_2$ solution is used to deposit Pd on the catalyst support, Pd would be in +2 oxidation state before reduction. Without intending to be bound by any particular theory, it is believed that Pd in +2 state would likely not offer the desired hydrogenating capability to the catalyst. The catalyst would need to be activated by treatment in a reducing atmosphere, e.g., an $H_2$-containing atmosphere, to obtain Pd in metallic state supported on the inorganic substrate, which would impart the desired hydrogenation capability to the catalyst.

The catalyst in the first state is then subjected to a multi-stage activation process. In certain embodiments, the activation process can be advantageously conducted in the same reactor as that used for the subsequent hydroalkylation step. In other embodiments, if desired, the activation process may be conducted in one or more separate reactors and the activated catalyst is subsequently transferred to the hydroalkylation reactor where it is used for its intended purpose.

In the treating step (b) of the present activation process, the catalyst in the first state is treated with hydrogen at a first temperature of at least 120° C. in the presence of a first atmosphere comprising hydrogen. In certain embodiments, the first temperature can be in the range from a lower limit of about 120° C., or about 130° C., or about 140° C., or about 150° C., or about 160° C., or about 170° C., or about 180° C., to an upper limit of about 320° C., or about 310° C., or about 300° C., or about 290° C., or about 280° C., or about 270° C., or about 260° C., or about 250° C., or about 240° C., or about 200° C., or about 190° C. The first duration for which the catalyst in the first state is treated ranges from a lower limit of about 5 minutes, or about 10 minutes, or about 15 minutes, or about 30 minutes, or about 1.0 hour, or about 2.0 hours, or about 4.0 hours, or about 8.0 hours, to an upper limit of about 48 hours, or about 40 hours, or about 32 hours, or about 24 hours, or about 16 hours, or about 12 hours, or about 8.0 hours, or about 4.0 hours, depending on factors such as, inter alia, the specific flow rate and composition of the first atmosphere, the specific first temperature, and the composition of the catalyst in the first state. Generally, the lower the first temperature, the longer the first duration is required to obtain a given desired level of catalyst activity. In certain embodiments, where the first temperature is about 300° C., a first duration of treating the catalyst in the first state of 0 to 2.0 hours would be sufficient. In other embodiments, where the first temperature is about 240° C., the first duration may be required to be from 2.0 to 4.0 hours to achieve substantially the same level of activity of the catalyst in a second state. While a long first duration, such as more than 4.0 hours, or more than 6.0 hours, or more than 8.0 hours, even 10 hours, could be used, excessive exposure of the catalyst to temperatures above 280° C. often leads to somewhat lower catalyst performance and hence is not desirable. In certain embodiments, hydrogen partial pressure in the first atmosphere can range from about 0.1 bar (10 kPa) to about 100 bar (10,000 kPa), such as from about 0.5 bar (50 kPa) to about 50 bar (5,000 kPa), for example, from about 1 bar (100 kPa) to about 5 bar (500 kPa).

The hydrogen gas present in the first atmosphere can react with the hydrogenating metal component, if in oxidized state, and reduce the metal into metallic state. As discussed above, the metallic metal would then provide the hydrogenating function to the catalyst assembly. The first atmosphere can be pure $H_2$ gas, or a mixture comprising $H_2$ and an inert gas, such as $N_2$. For example, an exemplary first atmosphere can comprise, in addition to $H_2$, $N_2$ and $CH_4$. Desirably, the first atmosphere comprises water at a concentration of at most 100 ppm, or at most 80 ppm, or at most 60 ppm, or at most 40 ppm, or at most 20 ppm, by mole. Furthermore, in certain embodiments, it is highly desired that the first atmosphere is a flowing stream of gas comprising water at a low concentration mentioned above. A dry first atmosphere in the form of a flowing stream can serve the additional function of drying the catalyst in the first state, which may comprise a substantial amount of water prior to activation using the process of the present disclosure, and stripping the water produced in situ as a result of the reduction of the metal in oxidized state and the water desorbed from the acid and inorganic oxide components. It is highly desired in certain embodiments that the first atmosphere comprises aromatic compounds (such as benzene) at a concentration of at most 500 ppm by mole, in certain embodiments at most 400 ppm, in certain embodiments at most 300 ppm, in certain other embodiments at most 200 ppm, in certain other embodiments at most 100 ppm, in certain other embodiments even at most 50 ppm, that may undergo hydrogenation and/or hydroalkylation at the first temperature in the presence of $H_2$.

After completion of the treating step (b) in the presence of the first atmosphere of the present activation process, the catalyst in the first state is converted into a catalyst in the second state having a hydroalkylation activity of HA1. The hydroalkylation activity HA1, if with respect to benzene, is measured under the conditions specified above. Afterwards, the catalyst in the second state is contacted with a first aromatic compound, such as benzene, and hydrogen under a first hydroalkylation condition effective to convert at least part of the first aromatic compound to a second aromatic compound having an alkyl group, such as cyclohexylbenzene, at a second temperature for a second duration. In certain embodiments, the second duration of this contacting step (c) can range from a lower limit of about 2.0 hours, or about 3.0 hours, or about 4.0 hours, or about 6.0 hours, or about 12 hours, or about 24 hours, to an upper limit of about 4000 hours, or about 2000 hours, or about 1000 hours, or about 500 hours, or about 300 hours, or about 200 hours, or about 100 hours, or about 80 hours, or about 60 hours, or about 40 hours, or about 32 hours, or about 24 hours. In various embodiments, the second temperature in the contacting step (c) can range from a lower limit of about 80° C., or about 90° C., or about 110° C., or about 120° C., or about 130° C., or about 140° C., or about 150° C., or about 180° C., to an upper limit of about 400° C., or about 360° C., or about 320° C., or about 300° C., or about 280° C., or about 250° C., or about 200° C. The first hydroalkylation condition include total pressure, $H_2$ partial pressure, reactor type, flow rates of the reactants, ratio of the various reactants in the feed material, and other parameters. The absolute pressure of the atmosphere used in the treating step (c) can range from a lower limit of about 100 kPa, or about 200 kPa, or about 300 kPa, to an upper limit of about 7,000 kPa, or about 5,000 kPa, or about 4,000 kPa, or about 3,000 kPa, or about 2,000 kPa, or about 1,000 kPa. In various embodiments, the first hydroalkylation condition of step (c) includes a molar ratio of $H_2$ to benzene ranging from a lower limit of about 0.15, or 0.20, or 0.30, or 0.40, or 0.50, or 0.60, or 0.80, or 0.90, or 1.00, to an upper limit of 15.00, or 14.00, or 12.00, or 10.00, or 8.00, or 6.00, or 4.00.

At the completion of the contacting step (c) of the activation process of the present disclosure, the catalyst in the second state is converted into a catalyst in the third state with a second hydroalkylation activity of HA2. The second hydroalkylation activity HA2, if with respect to benzene, is measured under the condition specified above. Depending on the first hydroalkylation condition, the second temperature and the second duration, HA2 may be comparable to HA1 or in certain embodiments HA2 is slightly lower than HA1. Prolonged use of a catalyst under use condition can lead to the loss of catalytic activity over time. The catalyst in the third state would normally contain, in addition to the acid component, the hydrogenating metal component, an optional metal oxide support, a small amount of the first aromatic compound used in step (c), and possibly a small amount of the second aromatic compound produced in step (c). In certain embodiments, step (c) is advantageously conducted in a reactor, such as an industrial reactor used for producing large quantity of the second aromatic compound, or in a relatively small reactor specifically designed and constructed for the purpose of activating the catalyst according to the process of the present disclosure. In certain embodiments, steps (b) and (c) are advantageously carried out in the same reactor.

Afterwards, in step (d) of the catalyst activation process of the present disclosure, the catalyst in the third state is further treated in the presence of a third atmosphere comprising $H_2$ and less than 30% by mole of the first aromatic compound at a third temperature for a third duration. This step (d) can be conducted in the same reactor used in step (b) or step (c), or both. Because the catalyst in the third state and the reactor used in step (d) can contain a small amount of the first aromatic compound and products of step (c), at the beginning of step (d), the third atmosphere may comprise a higher volume percentage of the first aromatic compound (such as, e.g., benzene, cyclohexylbenzene, and the like). In embodiments where the third atmosphere is a flowing stream of gas, as step (d) progresses, the volume percentage of the first aromatic compound present in the third atmosphere may decrease, and desirably eventually reaches a negligible level.

In the treating step (d), the third temperature can be in the range from a lower limit of about 160° C., or about 170° C., or about 180° C., or about 190° C., or about 200° C., to an upper limit of about 400° C., or about 380° C., or about 360° C., or about 340° C., or about 320° C., or about 310° C., or about 300° C., or about 290° C., or about 280° C., or about 270° C., or about 260° C., or about 250° C., or about 240° C., or about 220° C., or about 200° C., or about 190° C. The third duration for which the catalyst in the third state is treated ranges from a lower limit of about 5.0 minutes, or about 10 minutes, or about 15 minutes, or about 30 minutes, or about 1.0 hours, or about 2.0 hours, or about 4.0 hours, or about 8.0 hours, to an upper limit of about 48 hours, or about 40 hours, or about 32 hours, or about 24 hours, or about 16 hours, or about 12 hours, or about 8 hours, or about 4.0 hours, depending on factors such as, inter alia, the specific flow rate and composition of the third atmosphere, the specific third temperature, and the composition of the catalyst in the third state. Generally, the lower the third temperature, the longer the third duration is required to obtain a given desired level of catalyst activity. In certain embodiments, where the third temperature is about 300° C., a third duration of treating the catalyst in the third state of 0 to 2.0 hours would be sufficient. In other embodiments, where the third temperature is about 240° C., the third duration may range from 2.0 to 4.0 hours to achieve substantially the same level of activity of the catalyst in the fourth second state. While a long third duration, such as more than 4.0 hours, or more than 6.0 hours, or more than 8.0 hours, even more than 10 hours, could be used, excessive exposure of the catalyst to temperatures above 280° C. often leads to somewhat lower catalyst performance and hence is typically not desirable. In certain embodiments, hydrogen partial pressure in the third atmosphere can range from about 0.1 bar (10 kPa) to about 100 bar (10,000 kPa), such as from about 0.5 bar (50 kPa) to about 50 bar (5,000 kPa), for example from about 1.0 bar (100 kPa) to about 5.0 bar (500 kPa).

Similar to the first atmosphere, the third atmosphere can be a pure $H_2$ gas, or a mixture comprising $H_2$ and an inert gas, such as $N_2$. For example, an exemplary third atmosphere can comprise, in addition to $H_2$, $N_2$, $CH_4$, and the like. Desirably, the third atmosphere comprises water at a low concentration of at most 100 ppm, or at most 80 ppm, or at most 60 ppm, or at most 40 ppm, or at most 20 ppm, by mole. Furthermore, in certain embodiments, it is highly desired that the third atmosphere is a flowing stream of gas comprising water at a low concentration mentioned above. A dry third atmosphere in the form of a flowing stream can serve the additional function of stripping the catalyst in the third state, which may comprise a small amount of the first aromatic compound and reaction product of step (c).

At the completion of step (d), the catalyst in the third state is converted into a catalyst in the fourth state, which has a third hydroalkylation activity of HA3. The third hydroalkylation activity HA3, if with respect to benzene, is measured under the conditions specified above. Surprisingly, the present inventors found that HA3>HA1. In certain embodiments of the process of the present disclosure, (HA3−HA1)/HA1 ranges from a lower limit LL to an upper limit UL, where LL can be 0.05, 0.10, 0.15, 0.20, 0.25, 0.30, 0.40, 0.50, 0.60, 0.70, 0.80, or 0.90, and UL can be 0.10, 0.15, 0.20, 0.25, 0.30, 0.40, 0.50, 0.60, 0.70, 0.80, 0.90, 1.00, 1.50, or 2.00, provided LL≤UL. This increased activity after multiple-stage activation is a new phenomenon that has not been observed previously. In the past, after rejuvenation of a spent hydroalkylation catalyst by hydrogen treatment, the hydroalkylation activity of the catalyst could only be partially restored, i.e., one having ordinary skill in the art of catalysis in the hydroalkylation field would normally expect HA3<HA1.

The catalyst in the fourth state prepared according to the present disclosure can then be advantageously used in commercial hydroalkylation processes, such as step (e), in which a third aromatic compound, which may be the same as or different from the first aromatic compound used in step (c), is converted into a fourth, target aromatic compound having an alkyl group, such as the hydroalkylation of benzene to produce cyclohexylbenzene, under the second hydroalkylation condition. The second hydroalkylation condition include total pressure, $H_2$ partial pressure, reactor type, flow rates of the reactants, ratio of the various reactants in the feed material, and other parameters. The second hydroalkylation condition of the contacting step (e) may be the same as or different from the first hydroalkylation condition of the contacting step (c). In one embodiment, the first and third aromatic compounds in steps (c) and (e) are the same, e.g., both benzene, and the second and fourth aromatic compounds in steps (c) and (e) are the same, e.g., cyclohexylbenzene, and the first and second hydroalkylation conditions in steps (c) and (e) are the same. In this particular embodiment, the second/fourth aromatic compound from both steps (c) and (d) may be both the target product of the overall process.

The hydroalkylation reactions in the contacting steps (c) and (e) can be conducted in a wide range of reactor configurations including fixed bed, slurry reactors, and/or catalytic distillation towers. In addition, each of the hydroalkylation reactions (c) and (e) can be conducted in a single reaction zone or in a plurality of reaction zones, in which at least the hydrogen may be introduced to the reaction in stages.

The effluent produced the hydroalkylation step (e) may be subjected to additional steps such as separation of the fourth aromatic compound from the reaction effluent of step (e), and then further purification before it is used for its intended purpose. For example, in an embodiment where the third aromatic compound is benzene, and the fourth aromatic compound is cyclohexylbenzene, the target cyclohexylbenzene may be separated from the reaction mixture by, e.g., distillation. The unreacted feed material, including the third aromatic compound and $H_2$, can be recycled back to one or both of steps (c) and (e) to produce the third and/or fourth aromatic compounds.

The target fourth aromatic compound, e.g., cyclohexylbenzene, upon separation and optional additional purification, can be used as a solvent or the feed material for making another target material. For example, in embodiments where the fourth aromatic compound is cyclohexylbenzene, it may be fed to an oxidation reactor in the next step, where it is converted to cyclohexylbenzene hydroperoxide, which, in turn, is further subjected to cleavage reaction to produce phenol and cyclohexanone, two very useful industrial materials. Disclosure of the oxidation of alkyl aromatic compounds and subsequent cleavage reactions are provided in, e.g., WO2012/050751A1, WO2009/115276A1, and U.S. Patent Application Publication No. 2011/0301387, the relevant contents thereof are incorporated herein by reference. The hydroalkylation step (c) and/or (e) may be desirably integrated with one or more of the subsequent separation, purification, oxidation, and cleavage steps in a single facility in certain embodiments, or carried out in separate facilities, as the case may be.

The catalyst in the fourth state may be used in step (e) for a period ranging from several days to several years to several decades. It is common to observe degradation of the catalytic activity of a catalyst after such long service period due to various reasons including, but not limited to, accumulation of catalyst poison. Given that such catalysts may contain a substantial amount of expensive precious metal, it may be desired to further regenerate the catalyst to restore at least a portion of its original catalyst activity. Thus, in certain embodiments of the process of the present disclosure, upon completion of step (e), a catalyst in a fifth state having a fourth hydroalkylation activity HA4 is obtained, HA4<HA3, and the process further comprises a regeneration step (f) after step (e):

(f) treating the catalyst in the fifth state at a fifth temperature of at least 120° C. in a fifth atmosphere comprising hydrogen and less than 30% by mole of the first aromatic compound for a fourth duration to produce a catalyst in a sixth state having a fifth hydroalkylation activity HA5, where HA5>HA4.

In such embodiments including the regeneration step (f), the fifth atmosphere may be the same as, or different from, the third atmosphere in step (d), and the fifth temperature may be the same as, or different from, the third temperature in step (d), and the fourth duration may the same as, or different from, the third duration in step (d). Likewise, it is possible to conduct step (f) in a reactor the same as, or different from, the reactor used in step (d). At the end of the regeneration step (f), because the catalyst had been in service in step (e) for a long period of time, it is common to observe HA4<HA5<HA3. Thus, while some catalytic activity is restored at the end of step (f) relative to the end of step (e), it is common that the regenerated catalyst has a lower hydroalkylation activity than its peak, which is normally at the completion of step (d) but prior to the beginning of step (e).

Benzene Hydroalkylation Process

The use of the catalyst in the fourth state according to the present disclosure is now further illustrated by the specific embodiment of hydroalkylation of benzene as the third aromatic compound to produce cyclohexylbenzene as the fourth aromatic compound, below:

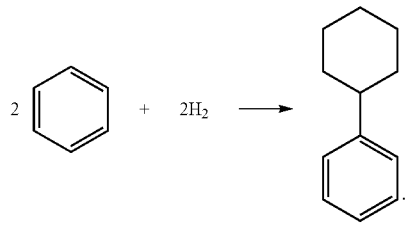 [SMILES: c1ccccc1 ; c1ccc(C2CCCCC2)cc1]

Any commercially available benzene feed can be used in the hydroalkylation step (e), but preferably the benzene has a purity level of at least 80 wt %, or at least 85 wt %, or at least 90 wt %, or at least 95 wt % or at least 99 wt %. In certain embodiments, the benzene feed can be diluted with inert components, like paraffins, without preventing the desired chemical transformation, but excessive amounts of diluents tend to increase process cost, and so are not desired in certain embodiments.

Similarly, although the source of hydrogen is not critical, it is desirable in certain embodiments that the hydrogen is at least 70 mol % pure, or at least 75 mol % pure, or at least 80 mol % pure, or at least 85 mol % pure, or at least 90 mol % pure, or at least 95 mol % pure at least 99 mol % pure. Advantageously, the feed hydrogen contains less than 50 mol % inert diluents, but hydrogen feeds with higher concentration of inert diluents can also be used to achieve meaningful conversion of the benzene feed.

Desirably in certain embodiments, the total feed to the hydroalkylation process contains less than 1000 ppm by weight, such as less than 500 ppm by weight, for example, less than 100 ppm by weight, water. In addition, the total feed to the hydroalkylation process should be substantially free of nitrogen and sulfur compounds, that is contain less than 100 ppm by weight, such as less than 10 ppm by weight, for example less than 1 ppm by weight, for example, less than 0.1 ppm by weight, for example, less than 0.01 ppm by weight, for example, less than 0.001 ppm by weight sulfur and less than 10 ppm by weight, such as less than 1 ppm by weight, for example, less than 0.1 ppm by weight, for example, less than 0.01 ppm by weight, for example, less than 0.001 ppm by weight nitrogen.

Hydrogen can be supplied to the hydroalkylation step over a wide range of values, but is desirably arranged in certain embodiments such that the molar ratio of hydrogen to benzene in the hydroalkylation feed is from about 0.15:1 to about 15:1, such as from about 0.4:1 to about 4:1, for example, from about 0.4 to about 0.9:1. Advantageously, the hydrogen content in the feed is below that necessary to achieve 100% conversion of benzene to cyclohexane, or even below that is necessary to achieve 100% conversion of benzene to cyclohexylbenzene to increase hydroalkylation selectivity and decrease the potential of temperature runaway.

In addition to the benzene and hydrogen, a diluent, which is substantially inert under hydroalkylation conditions, may be supplied to the hydroalkylation reaction. In certain embodiments the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of useful diluents are decane and cyclohexane. Cyclohexane is an advantageous diluent in certain embodiments since it is an unwanted by-product of the hydroalkylation reaction.

Although the amount of diluent is not narrowly defined, desirably the diluent present in the liquid hydroalkylation feed is less than 90 wt %, or less than 50 wt %, or less than 25 wt %, or less than 10 wt %, or less than 5 wt %, or less than 1 wt % of the feed.

The benzene hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen may be introduced to the reaction in stages. Suitable reaction temperatures are from about 100° C. to about 400° C., such as from about 125° C. to about 250° C., while suitable reaction pressures are from about 100 kPa to about 7,000 kPa, such as from about 500 kPa to about 5,000 kPa.

The invention will now be more particularly described with reference to the following non-limiting examples.

EXAMPLES

In the examples, a series of hydroalkylation tests were performed in a down-flow 0.5 inch (12.7 mm) diameter stainless steel fixed bed reactor that was equipped with a three-point thermocouple positioned at the center of the reactor tube. The 4.5 inch (114.3 mm) long catalyst bed was positioned to ensure that three thermocouples (placed 2 inch (50.8 mm) apart) measured the temperatures at the inlet, outlet, and the center of the catalyst bed. In order to reduce the volumetric heat release and thus to afford more isothermal operations, the catalyst was diluted with quartz. The diluent also enhanced the even distribution of the reactants in the catalyst bed. Neat quartz was used at either side of the catalyst bed. The quartz served to preheat and evenly distribute the feed at the feed inlet side and to hold the catalyst bed at the exit side, the latter of which was at the bottom of the reactor (downflow).

The reactor was encased in a 6 inch (152.4 mm) long and 1 inch (25.4 mm) diameter brass sleeve that was centered along the catalyst bed to improve its temperature control. Housed in the brass sleeve were the three thermocouples positioned at the two ends and the center of the catalyst bed. The reactor was heated by a three-zone clam-shell electrical furnace. During steady-state operations, the temperatures of the three furnace zones were controlled by utilizing the feedback from the three thermocouples in the brass sleeve of the reactor. The catalyst bed temperatures at the three thermocouples were typically within 2° C. of the set value. The reported reaction temperatures ($T_{rxn}$) were calculated as the weighted average of the three thermocouple measurements ($T_{inlet}$, $T_{middle}$, $T_{outlet}$) by the following formula:

$$T_{rxn} = (T_{inlet} + 2T_{middle} + T_{outlet})/4.$$

The catalysts in all experiments nominally comprised 0.15 wt % Pd supported on alumina-bound MCM-49 with an alumina/MCM-49 weight ratio of 20/80. The catalyst was received in its calcined form as 1/20 inch (1.27 mm) extrudate and was stored in closed plastic bottles. Before charging to the reactor, the catalyst extrudates were broken up and sized to a length/diameter (L/D) ratio of near one (14-20 mesh) to afford the reactor beds with proper hydrodynamics. As mentioned above, the catalyst was also diluted with quartz that on one hand reduced volumetric catalyst charge and thus volumetric heat release while also improving the desired plug-flow characteristic of the reactant stream passing through the catalyst bed.

In an exemplary hydroalkylation test, 2 g of 14-20 mesh catalyst diluted with 6 g quartz was charged into the reactor. The moisture content of the as-loaded catalyst was nominally 12 wt %, thus the dry catalyst load was 1.76 g. After pressure testing, the catalyst was hydrogen treated at 50 psig (345 kPa gauge) by ramping its temperature up to the target maximum value at 60° C./hour ramp rate then holding it there for the prescribed time. The hydrogen flow rate in all tests was 169 sccm (standard cubic centimeter per minute) corresponding to a 2028 volume $H_2$/volume catalyst/hour (or 2028/h) gas hourly space velocity (GHSV). The initial hydrogen treatment (step (b)) was finished by letting the catalyst cool down to near the hydroalkylation temperature (145° C.) while keeping the pressure and hydrogen flow rate unchanged. The catalyst then was brought on stream by first increasing the pressure to 165 psig (1138 kPa gauge), then reducing the hydrogen flow rate to 18 sccm and introducing benzene at 1 mL/min flow rate (step (c)). This condition was maintained for 1 hour to ensure that the catalyst bed was properly wetted after which the benzene flow rate was reduced to 0.096 mL/min corresponding to a nominal 0.7 mol $H_2$/mol benzene feed composition and 2.5 weight benzene/weight catalyst/h (or 2.5/h) weight hourly space velocity (WHSV) on an as-loaded basis (i.e., catalyst with a nominal moisture content of 12 wt %).

After letting the reactor line out for about 6.0 hours, the product effluent was periodically directed to a chilled knock out vessel held at −5° C. and liquid samples were collected then analyzed by a gas chromatograph equipped with a flame-ionization detector (FID). The response factors for the various product components were determined either using blends of authentic samples or by using factors published in the J. of Gas Chromatography in February 1967, pg. 68 by W. A. Dietz. Calibrations were checked by analyzing gravimetrically prepared calibration blends. Benzene conversion and product selectivity were determined from the normalized FID areas by applying the calibration response factors.

To perform subsequent hydrogen activation treatment(s), the catalyst bed was first dried by stopping the benzene flow, dropping the reactor pressure to ambient, increasing the hydrogen flow to 200 sccm (2400/h GHSV), and holding this condition for 3.0 hours. After drying the catalyst bed, the pressure was increased to 50 psig (345 kPa gauge), the hydrogen flow was set to 169 sccm (2028/h GHSV). The temperature then was ramped to the target maximum value and held there for the prescribed hold time. The second hydrogen treatment (step (d)) was finished by letting the catalyst cool down to the hydroalkylation temperature (145° C.) while keeping the pressure and hydrogen flow rate unchanged. The catalyst then was brought back on stream by first increasing the pressure to 165 psig (1138 kPa gauge), then reducing the hydrogen flow rate to 18 sccm and introducing benzene at 1 mL/min flow rate. This condition was maintained for 1 hour to ensure that the catalyst bed was properly wetted after which the benzene flow rate was reduced to 0.096 mL/min corresponding to a nominal 0.7 mol $H_2$/mol benzene feed composition and 2.5 weight benzene/weight catalyst/h (or 2.5/h) WHSV on an as-loaded basis (i.e., catalyst with a nominal moisture content of 12 wt %) (step (e)).

Examples 1 to 3

The three experiments summarized in Table 1 demonstrate the activity increasing effect of the currently disclosed staged activation process while both the first and second hydrogen treatments (steps (b) and (d)) performed within the preferred ranges of maximum treatment temperatures and durations. Examples 1 and 2 were performed at identical conditions in two separate reactors using the same catalyst batch and following the same sequence of conditions. These two runs demonstrate the reproducibility of the activity gain achievable by the currently disclosed staged activation process.

As shown in Table 1, the initial hydrogen treatment (step (b), corresponding to the prior art single-stage activation process) was performed by ramping the catalyst bed temperature to 300° C. (the first temperature) and holding that temperature nominally for 2.0 hours (the first duration). Flow and pressure conditions were as described in the generic hydrogen treatment procedure above. After the initial hydrogen treatment, the catalyst was put on hydroalkylation (HA) stream (step (c)). After initial line out (see results in Table 1 at 117 h on HA stream), benzene conversion (the first hydroalkylation activity, HA1) was 34% in both reactors. By 285/290 hours on HA stream (time on stream, hereinafter "TOS"), the conversions in Examples 1 and 2 were 35% and 37% (the second hydroalkylation activity, HA2), respectively, indicating that the catalyst performance was essentially lined out by 117 hours TOS.

The second hydrogen treatment (step (d)) was performed in both Examples 1 and 2 after the catalyst charges were on HA stream for 291 hours (step (c)). After this second hydrogen treatment (step (d)), benzene conversions (the second hydroalkylation activity) significantly increased and lined out at 44% and 48% (as indicated by readings at 505 hours TOS in Table 1), respectively.

Finally, the catalysts were exposed to a third hydrogen treatment after 628 hours on HA stream (i.e., a third $H_2$ treatment after step (e)). As the results in Table 1 demonstrate, this third $H_2$ treatment did not result in further activity increase (see lined-out benzene conversion results in Table 1 measured at 896 and 897 hours TOS in Examples 1 and 2, respectively).

These results thus demonstrate that (i) a sequence of hydrogen treatment (step (b)) followed by putting the catalyst on hydroalkylation stream (step (c)) which then followed by a second hydrogen treatment (step (d)) brings catalytic activity above its fresh levels obtained after the initial hydrogen treatment (step (b)), corresponding to the conventional activation process) and (ii) additional (third or more) hydrogen treatments after step (d) are not necessary to attain increased activity. In fact, the disclosed three-step sequence of (1) hydrogen treatment step (b); (2) benzene HA step (c); and (3) hydrogen treatment step (d) is sufficient to achieve maximum activity. A comparison of the results from Examples 1 and 2 also demonstrates that the benefits of the three-step staged activation process of the current disclosure are reproducible.

TABLE 1

| | $H_2$ Treatment | | | Hydroalkylation | |
| --- | --- | --- | --- | --- | --- |
| Example | At TOS (hour) | Maximal Temperature (° C.) | Duration (hour) | At TOS (hour) | Benzene Conversion (%) |
| 1 | 0 | 300 | 2.2 | 117 | 34 |
| 1 | 0 | 300 | 2.2 | 285 | 35 |
| 1 | 291 | 300 | 2.3 | 505 | 44 |
| 1 | 628 | 300 | 2.2 | 896 | 44 |
| 2 | 0 | 300 | 2.2 | 117 | 34 |
| 2 | 0 | 300 | 2.2 | 290 | 37 |
| 2 | 291 | 300 | 2.3 | 505 | 48 |
| 2 | 628 | 300 | 2.2 | 897 | 47 |
| 3 | 0 | 240 | 10.6 | 146 | 32 |
| 3 | 146 | 240 | 10.6 | 245 | 39 |
| 3 | 249 | 300 | 2.7 | 399 | 39 |

Example 3 demonstrates the benefits of the three-step staged activation sequence of the current disclosure at lower hydrogen treatment temperatures. As the results in Table 1 show, benzene conversion increased from 32% after the first hydrogen treatment (step (b)) to 39% by completing the three-step staged activation process of the current disclosure. As in Examples 1 and 2, the third hydrogen treatment performed after step (e) does not yield further activity gain even when performed at higher temperature (300° C.).

Note that conventional activation processes only include the first hydrogen treatment. Thus in the first demonstration runs, i.e., in Examples 1 and 2, the three-step activation process of the current disclosure increased benzene conversion over the prior art by approximately 10% (absolute). In Example 3, applying lower hydrogen treatment temperatures, the conversion gain over the prior art one-step activation process was 7% (absolute).

Examples 4 and 5

Examples 1 to 3 demonstrate that the second hydrogen treatment of the currently disclosed three-step activation process increased catalytic activity to well above the activity observed after the first hydrogen treatments. Examples 4 and 5 test whether the same increase in activity can be achieved by increasing the severity of the initial hydrogen treatment (i.e., applying longer treat time and/or higher treat temperature). The results are summarized in Table 2.

TABLE 2

| | $H_2$ Treatment | | | Hydroalkylation | |
| --- | --- | --- | --- | --- | --- |
| Example | At TOS (hour) | Maximal Temperature (° C.) | Duration (hour) | At TOS (hour) | Benzene Conversion (%) |
| 4 | 0 | 300 | 6.3 | 313 | 32 |
| 4 | 319 | 300 | 2.5 | 465 | 35 |
| 5 | 0 | 350 | 6.5 | 313 | 25 |
| 5 | 319 | 300 | 3.0 | 465 | 32 |

In Example 4, the catalyst was initially treated in hydrogen at 300° C. for 6.0 hours (step (b)). Note that this treatment effectively combined, or even slightly exceeded, the total high temperature hydrogen treatment time employed in Examples 1 and 2. As the results in Table 2 show, this more severe initial activation by $H_2$ treatment did not yield improved activity. In fact, it afforded a catalyst that gave 32% benzene conversion at 145° C., 165 psig (1138 kPa gauge), 0.7 mol $H_2$/mol benzene, and 2.5/h WHSV (see the conversion in Table 2 after the first activation performed at 0 h TOS), which is somewhat below the conversion achieved when the same catalyst was initially treated for only 2.0 hours at 300° C. (see Table 1, Examples 1 and 2 after activation at 0 h TOS). It also falls far below the 44-48% benzene conversion achieved with the three-step staged activation process of the current disclosure at the completion of step (d) (see Table 1, Examples 1 and 2 after second hydrogen treatment at 291 h TOS). While performing a second hydrogen treatment (step (d)) did increase benzene conversion to 35% (see the conversion in Table 2 after the second hydrogen treatment performed at 319 h TOS), the achieved activity was below that achieved after the second hydrogen treatment (step (c)) in the comparable Examples 1 and 2. This demonstrates that a three-step activation process improves activity, but the ultimate conversion result falls short of the demonstrated maximum when the first hydrogen treatment is too severe (e.g., where the first duration was as long as 6.0 hours).

In Example 5, the severity of the first hydrogen treatment was further increased by ramping the catalyst to a maximum temperature of 350° C. (the first temperature) and holding it there for 6.0 hours (the first duration). The outcome was directionally the same as in Example 4: the more severe initial hydrogen treatment (step (b)) resulted in a permanently lower hydroalkylation activity. In fact, the activity was even lower than in Example 4 because the severity of the initial treatment was compounded not only by the prolonged first duration at the maximum treatment temperature, but also by increasing the maximum first temperature. Although the three-step staged activation process again resulted in an activity improvement over the catalytic activity achieved by a one-step hydrogen treatment (compare results in Table 2 obtained after 0 h and 319 h TOS), hydroalkylation activity was below that achieved after milder initial treatments (step (b)) as in Examples 1 to 3.

Thus, a comparison of benzene conversions after the first hydrogen treatments (step (b), activations at 0 h TOS) in Examples 1 and 2 with those in Examples 4 and 5 shows that increasing the severity of the initial hydrogen treatment can permanently reduce the maximum attainable hydroalkylation activity even when a second hydrogen treatment (step (d)) according to the three-step activation process of the current disclosure is applied. Note that the currently-disclosed three-step staged activation process still increased hydroalkylation activity though the conversions achieved were lower than what was achieved after the three-step activations in Example 1. In conclusion, the examples demonstrate the unexpected, significant benefits of the currently-disclosed three-step activation process. In addition, the examples demonstrate that (i) the level of hydroalkylation activity achievable by the currently-disclosed three-step staged activation process cannot be achieved by increasing the severity of the prior-art single-step activation process alone, and (ii) excessive hydrogen treatment times and temperatures do not improve performance and sometimes can permanently reduce catalytic activity, although applying the second hydrogen treatment of the currently disclosed activation process still improves catalytic performance.

Those having ordinary skill in the art, in the light of the disclosure herein, will readily understand that various modifications and adaptations can be made to the various aspects and embodiments of the present disclosure without departing from the scope and spirit of the invention as claimed.

The invention claimed is:

1. A process for activating a hydroalkylation catalyst, the process comprising:
   (a) providing a hydroalkylation catalyst in a first state comprising an acid component and a hydrogenating metal component;
   (b) treating the catalyst in the first state at a first temperature of at least 120° C. in a first atmosphere comprising hydrogen and at most 5% by mole of an aromatic compound for a first duration to produce a catalyst in a second state having a first hydroalkylation activity HA1;
   (c) contacting the catalyst in the second state with a first aromatic compound and a second atmosphere comprising hydrogen under a first hydroalkylation condition at a second temperature for a second duration effective to convert at least part of the first aromatic compound into a second aromatic compound comprising an alkyl group, and thereby obtaining a catalyst in a third state having a second hydroalkylation activity HA2, where HA2 is no lower than HA1, the second duration ranges from at least 0.5 hour to 300 hours, and the second temperature is in a range from 100° C. to 400° C.; and
   (d) treating the catalyst in the third state at a third temperature of at least 160° C. in a third atmosphere comprising hydrogen and less than 30% by mole of the first aromatic compound for a third duration to produce a catalyst in a fourth state having a third hydroalkylation activity HA3, where HA3>HA1.

2. The process of claim 1, wherein (HA3−HA1)/HA1≥0.05.

3. The process of claim 1, wherein at least one of the following conditions is met:
   (i) in the treating step (b), the first atmosphere comprises at most 1% by mole of all aromatic compounds; and
   (ii) in the treating step (d), the third atmosphere comprises less than 10% by mole of the first aromatic compound.

4. The process of claim 1, wherein the first atmosphere has an $H_2$ partial pressure in a range from 100 kPa to 500 kPa.

5. The process of claim 1, wherein in the treating step (b), the first atmosphere is a flowing stream of gas comprising water at a concentration of less than 100 ppm by mole.

6. The process of claim 1, wherein in the treating step (d), at least one of the following conditions is met:
   (i) the third atmosphere is a flowing stream of gas comprising water at a concentration of less than 100 ppm by mole; and
   (ii) the third atmosphere comprises at least 80% by mole of $H_2$.

7. The process of claim 1, wherein the first aromatic compound is benzene.

8. The process of claim 1, wherein in the treating step (b), the first duration ranges from about 0.5 hour to about 50 hours.

9. The process of claim 8, wherein in the treating step (b), the first temperature is in a range from about 140° C. to about 360° C.

10. The process of claim 1, wherein in the treating step (d), at least one of the following conditions is met:
    (i) the third duration ranges from about 0.5 hour to about 24 hours; and
    (ii) the third temperature is in a range from about 180° C. to about 360° C.

11. The process of claim 1, wherein the hydrogenating metal component is selected from Re, Fe, Ru, Os, Co, Rh, Ir, Ni, Pd, Pt and mixtures and combinations of at least two thereof.

12. The process of claim 1, wherein at least one of the following conditions is met:
    (i) the hydrogenating metal component comprises palladium; and
    (ii) the acid component comprises a MWW zeolite type molecular sieve.

13. A process for producing a cycloalkyl substituted aromatic compound, the process comprising:
    (a) providing a hydroalkylation catalyst in a first state comprising an acid component and a hydrogenating metal component;
    (b) treating the catalyst in the first state at a first temperature of at least 120° C., in a first atmosphere comprising hydrogen and at most 5% by mole of an aromatic compound for a first duration to produce a catalyst in a second state having a first hydroalkylation activity HA1;
    (c) contacting the catalyst in the second state with a first aromatic compound and a second atmosphere comprising hydrogen under a first hydroalkylation condition at a second temperature for a second duration effective to convert at least part of the first aromatic compound into a second aromatic compound comprising an alkyl group, and thereby obtaining a catalyst in a third state having a second hydroalkylation activity HA2, where HA2 is no lower than HA1, the second duration ranges from at least 0.5 hour to about 300 hours, and the second temperature is in a range from 100° C. to about 400° C.;
    (d) treating the catalyst in the third state at a third temperature of at least 160° C. in a third atmosphere comprising hydrogen and less than 30% by mole of the first aromatic compound for a third duration to produce a catalyst in a fourth state having a third hydroalkylation activity HA3, where HA3>HA1; and
    (e) contacting the catalyst in the fourth state in a hydroalkylation reactor with a third aromatic compound and hydrogen under a second hydroalkylation condition effective to convert at least part of the third aromatic compound to a fourth aromatic compound comprising a cycloalkyl group.

14. The process of claim 13, wherein (HA3−HA1)/HA1≥0.05.

15. The process of claim 13, wherein at least one of the following conditions is met:
    (i) in the treating step (b), the first atmosphere comprises at most 1% by mole of all aromatic compounds; and (ii) in the treating step (d), the third atmosphere comprises less than 10% by mole of the first aromatic compound.

16. The process of claim 13, wherein the first atmosphere has an $H_2$ partial pressure in a range from 100 kPa to 500 kPa.

17. The process of claim 13, wherein in the treating step (b), the first atmosphere is a flowing stream of gas comprising water at a concentration of less than 100 ppm by mole.

18. The process of claim 13, wherein in the treating step (d), at least one of the following conditions is met:
(i) the third atmosphere is a flowing stream of gas comprising water at a concentration of less than 100 ppm by mole; and
(ii) the third atmosphere comprises at least 80% by mole of $H_2$.

19. The process of claim 13, wherein in the treating step (b), at least one of the following conditions is met:
(i) the first duration ranges from about 0.5 hour to about 50 hours; and
(ii) the first temperature is in a range from about 140° C. to about 360° C.

20. The process of claim 13, wherein in the treating step (d), at least one of the following conditions is met:
(i) the third duration ranges from about 0.5 hour to about 24 hours; and
(ii) the third temperature is in a range from about 180° C. to about 360° C.

21. The process of claim 13, wherein at least one of the following conditions is met:
(i) the hydrogenating metal component comprises palladium; and
(ii) the acid component comprises a MWW zeolite type molecular sieve.

22. The process of claim 13, wherein the first aromatic compound and the third aromatic compound are identical, and the second aromatic compound and the fourth aromatic compound are identical.

23. The process of claim 13, wherein the first aromatic compound and the third aromatic compound are benzene, and the second aromatic compound and the fourth aromatic compound are cyclohexylbenzene.

24. The process of claim 13, wherein steps (b), (c), (d), and (e) are carried out in a hydroalkylation reactor.

25. The process of claim 13, wherein at the end of step (e), a catalyst in a fifth state having a fourth hydroalkylation activity HA4 is obtained, HA4<HA3, and the process further comprises a step (f) after step (e):
(f) treating the catalyst in the fifth state at a fifth temperature of at least 120° C. in a fifth atmosphere comprising hydrogen and less than 30% by mole of the first aromatic compound for a fourth duration to produce a catalyst in a sixth state having a fifth hydroalkylation activity HA5, where HA5>HA4.

* * * * *